(12) United States Patent
Ueno

(10) Patent No.: US 8,924,188 B2
(45) Date of Patent: Dec. 30, 2014

(54) METHOD FOR SIMULATING DISPERSION OF FILLERS IN HIGH POLYMER MATERIAL

(71) Applicant: Sumitomo Rubber Industries, Ltd., Kobe (JP)

(72) Inventor: Shinichi Ueno, Kobe (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 11 days.

(21) Appl. No.: 13/858,970

(22) Filed: Apr. 9, 2013

(65) Prior Publication Data

US 2013/0332124 A1 Dec. 12, 2013

(30) Foreign Application Priority Data

Jun. 8, 2012 (JP) .................. 2012-131311

(51) Int. Cl.
*G06F 17/50* (2006.01)

(52) U.S. Cl.
CPC ........ *G06F 17/5009* (2013.01); *G06F 17/5095* (2013.01)
USPC .................................................. 703/2; 703/6

(58) Field of Classification Search
CPC ....................................................... G06F 17/50
USPC .......................................................... 703/2, 6
See application file for complete search history.

(56) References Cited

U.S. PATENT DOCUMENTS

| | | | |
|---|---|---|---|
| 2013/0238302 A1* | 9/2013 | Ueno | 703/6 |
| 2013/0311155 A1* | 11/2013 | Ueno | 703/6 |

FOREIGN PATENT DOCUMENTS

JP 2006-064658 A 3/2006

OTHER PUBLICATIONS

Allegra G et al: "Theories and simulations of polymer-based nanocomposites: From chain statistics to reinforcement"; Progress in Polymer Science, Pergamon Press, Oxford, GB, vol. 33, No. 7, Jul. 1, 2008; XP023906890; pp. 683-731.

D. Brown et al.; "Effect of Filler Particle Size on the Properties of Model Nanocomposites"; vol. 41, No. 4, Feb. 1, 2008; XP055082941; pp. 1499-1511.

Guido Raos et al: "Computational Experiments on Filled Rubber Viscoelasticity: What is the Role of Particle-Particle Interactions?", vol. 39, No. 19, Sep. 1, 2006; XP055069961; pp. 6744-6751.

Raos G et al: "Nonequilibrium simulations of filled polymer networks: Searching for the origins of reinforcement and nonlinearity"; Journal of Chemical Physics, American Institute of Physics, New York, NY, US, vol. 134, No. 5, Feb. 7, 2011; XP009172858; pp. 54902/1-14.

\* cited by examiner

*Primary Examiner* — Thai Phan
(74) *Attorney, Agent, or Firm* — Birch, Stewart, Kolasch & Birch, LLP

(57) ABSTRACT

A computerized method for simulating dispersion of fillers in a high polymer material comprises: a simulation step in which filler models and polymer models are disposed in a predetermined virtual space and a molecular dynamics calculation is made thereon; and an outputting step in which the dispersion state of the filler models is output based on results of the simulation step, wherein the filler model represents a plurality of filler particles one of which is defined as a most influential particle for which a largest cutoff distance is defined, and the outputting step includes a rendering step in which, as regards the filler models in the virtual space, only the most influential particles are rendered.

5 Claims, 16 Drawing Sheets

METHOD FOR SIMULATING DISPERSION OF FILLERS IN HIGH POLYMER MATERIAL

BACKGROUND OF THE INVENTION

The present invention relates to a computerized method for simulating the dispersion of fillers in a high polymer material, more particularly to a fast procedure for rendering a filler dispersion state.

High polymer materials such as compounded rubber used in vehicle tires usually contain fillers such as carbon black and silica. It is well known in the art that the dispersion of fillers in a compounded rubber exerts a strong influence on properties, e.g. strength of the rubber.

In recent years, in order to evaluate the dispersion of fillers in a high polymer material, various computerized simulation (numerical calculation) methods have been proposed.

In this kind of simulation method, filler models of fillers and polymer models of a high polymer material are defined, and a molecular dynamics (MD) calculation is performed on the filler models and polymer models placed or set in a predetermined virtual space. Then, from the results of the simulation, the filler models and polymer models are rendered in order to evaluate the dispersion of the fillers with the naked eye.

Therefore, this method has the following problems. First of all, the rendering of the filler models and polymer models requires a very long time.

Further, even when the rendered three-dimensional image of the filler models and polymer models is viewed from any direction, the filler models and polymer models are seen as being overlapped with each other. Therefore, it is difficult to exactly know how the filler models are dispersed.

SUMMARY OF THE INVENTION

It is therefore, an object of the present invention to provide a method for simulating the dispersion of fillers in a high polymer material which can render a dispersion state of the fillers at short times, in an easily recognizable way.

According to the present invention, a computerized method for simulating the dispersion of fillers in a high polymer material, comprises a filler model defining step in which filler models of the fillers are defined, wherein each of the filler models represents a plurality of filler particles, a polymer model defining step in which polymer models of the high polymer material are defined, wherein each of the polymer models represents one or more polymer particles, a potential defining step in which, between the particles inclusive of the filler particles and the polymer particles, potentials such that when the distance between the concerned particles is decreased under a predefined cutoff distance, a mutual interaction occurs therebetween, are defined, wherein one of the filler particles in each filler model is defined as a most influential particle for which a largest cutoff distance is defined, a simulation step in which a molecular dynamics calculation is performed on the polymer models and the filler models placed in a predetermined virtual space, and an outputting step in which, based on results obtained through the simulation step, the dispersion of the filler models is output, wherein the outputting step includes a rendering step in which the filler particles other than the most influential particles are hidden whereas the most influential particles of the filler models in the virtual space are rendered to present the state of the dispersion of the filler models.

The method according to the present invention may be provided with the following features (I)-(III):

(I) the outputting step further includes, before the rendering step, a step in which a radial distribution function of the most influential particles of the filler models is calculated, and in the rendering step, each of the most influential particles is rendered as a sphere having a radius R of not less than a value Rmin and not more than a value Rmax, wherein the value Rmin is one half of a shortest distance between the most influential particles obtained from the radial distribution function, and the value Rmax is given by the following expression (1)

$$Rmax = (V/N)^{1/3}/2 \qquad (1)$$

where
V is the volume of the virtual space, and
N is the number of the most influential particles existing in the virtual space;

(II) the filler particles of each filler model are a single center filler particle and at least four surface filler particles whose centers are positioned on a spherical surface whose center coincides with a center of the center filler particle, equilibrium lengths are respectively defined between the center filler particle and the surface filler particles and between the surface filler particles, and the center filler particle is the most influential particle;

(III) the cutoff distance between the center filler particles is larger than the sum of the radius of the spherical surface and the cutoff distance between the surface filler particles.

Therefore, in a filler model, a potential from the outside of the filler model acts on the most influential particle prior to any other filler particles. In the molecular dynamics calculation, the most influential particle is taken as the representative point of the filler model. If migrations of the most influential particles are increased, the filler models can be considered as being dispersed widely. Therefore, in the method according to the present invention, only the most influential particles are rendered to show the state of the dispersion of the filler models. Accordingly, the filler dispersion state can be rendered at short times, in an easily recognizable way.

DESCRIPTION OF THE PREFERRED EMBODIMENTS

An embodiment of present invention will now be described in detail in conjunction with accompanying drawings.

The simulation method according to the present invention is a method for simulating and rendering the dispersion state of fillers in a high polymer material by the use of a computer 1. Here, the term "high polymer material" is intended to include at least rubber, resin and elastomer.
The term "filler" is intended to include at least carbon black, silica and alumina.

Figure 1:
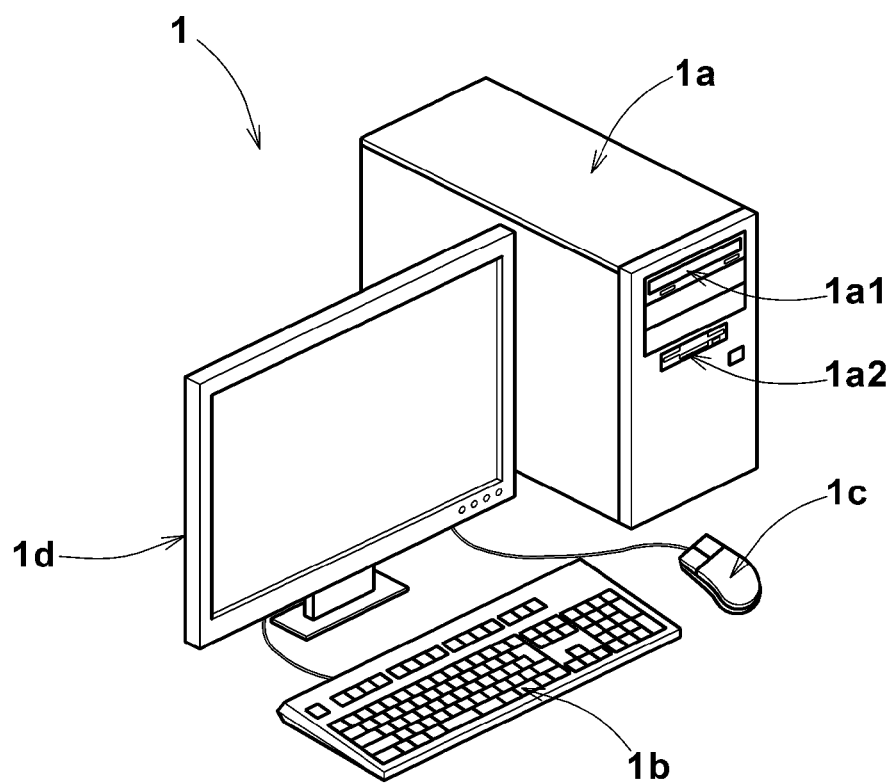
FIG. 1 is a perspective view of a computer system implementing a simulation method as an embodiment of the present invention.

As shown in FIG. 1 for example, the computer 1 comprises a main body 1a, a keyboard 1b, a mouse 1c and a display 1d. The main body 1a comprises an arithmetic processing unit (CPU), ROM, work memory, storage devices such as magnetic disk, disk drives 1a1 and 1a2 and the like. In the storage device, programs/software for carrying out the simulating method are stored.

Figure 2:
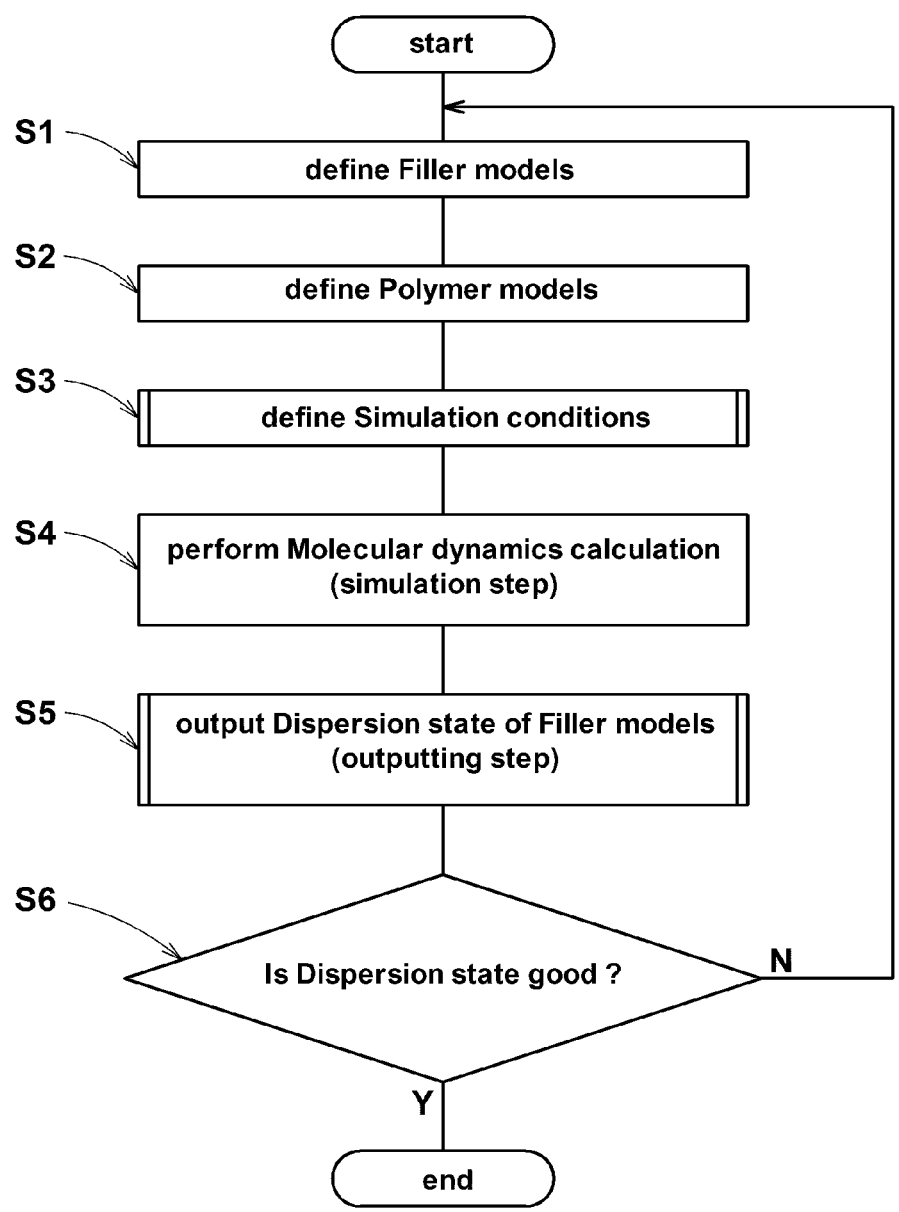
FIG. 2 is a flow chart of the simulation method in this embodiment.

FIG. 2 shows a flowchart of the simulation method as an embodiment of the present invention.

In this method, firstly, filler models 3 of the fillers are defined. (step S1).

Figure 3:
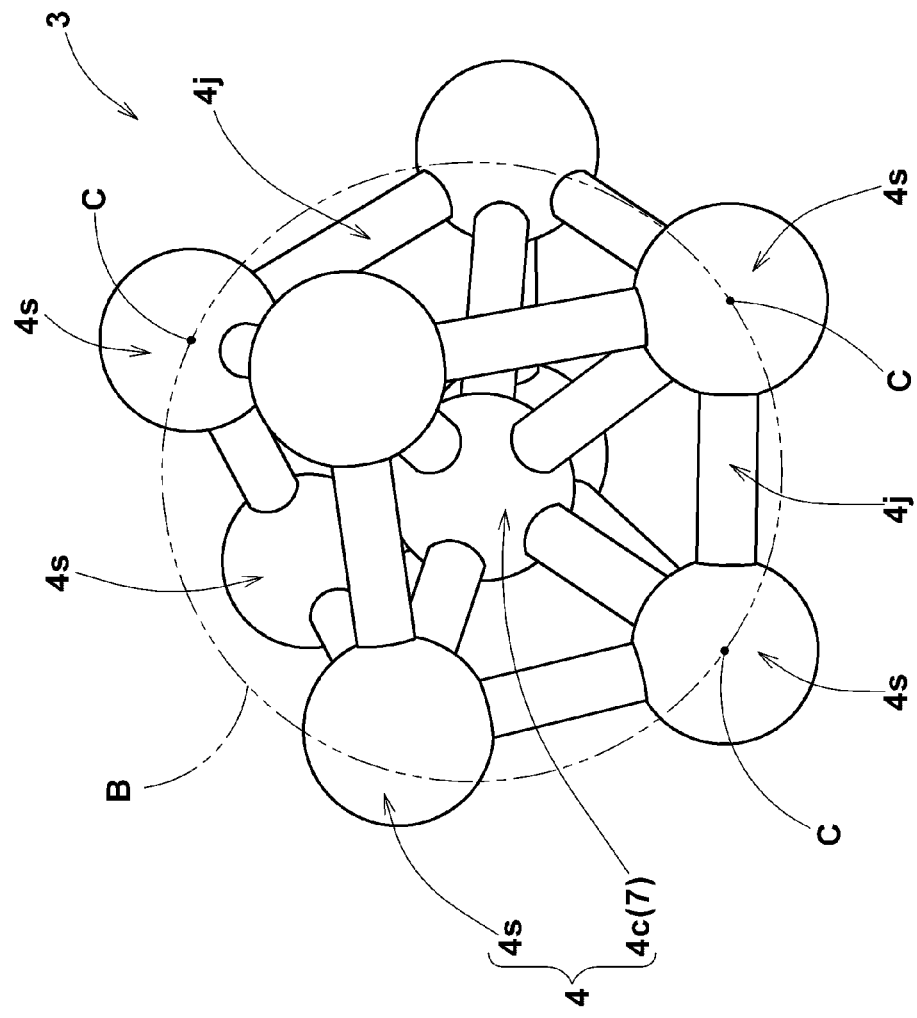
FIG. 3 is a diagram showing a filler model.

In this step S1, as shown in FIG. 3, each filler model 3 is defined to represent a plurality of filler particles 4 (e.g. carbon particles), wherein each of the filler particles 4 is a sphere having a certain diameter.

Incidentally, the filler model 3 corresponds to numerical data (inclusive of the mass, volume, diameter and initial coordinates of each of the filler particles 4) necessary to deal with the fillers by the molecular dynamics. Such numerical data are entered and stored in the computer 1.

The filler particles 4 constituting each filler model 3 are a single center filler particle 4c, and at least four in this example eight surface filler particles 4s, wherein the centers C of the surface filler particles 4s are positioned on a spherical surface B of which center coincides with the center of the center filler particle 4c.

In each filler model 3, between the center filler particle 4c and the surface filler particles 4s and also between the surface filler particles 4s, there are provided joining chains 4j on which equilibrium lengths are respectively defined.

Here, the equilibrium lengths are the bond distances between the center filler particle 4c and the surface filler particles 4s and between the surface filler particles 4s when the relative positions of the surface filler particle 4s on the spherical surface B become steady. If the bond distance is changed, it revert to the equilibrium length by the joining chain 4j so as to become a steady state.

Further, the center filler particle 4c and three or more surface filler particles 4s in each filler model 3 are arranged so as not to locate in the same plane or one plane.

In the filler model 3 in this example, the center filler particle 4c and the surface filler particles 4s are bonded, keeping their relative positions. The surface filler particles 4s are positioned at the vertices of a polyhedron, and the center filler particle 4c is positioned at the center of the polyhedron.

Next, polymer models 5 of the high polymer material are defined. (step S2)

Figure 4:
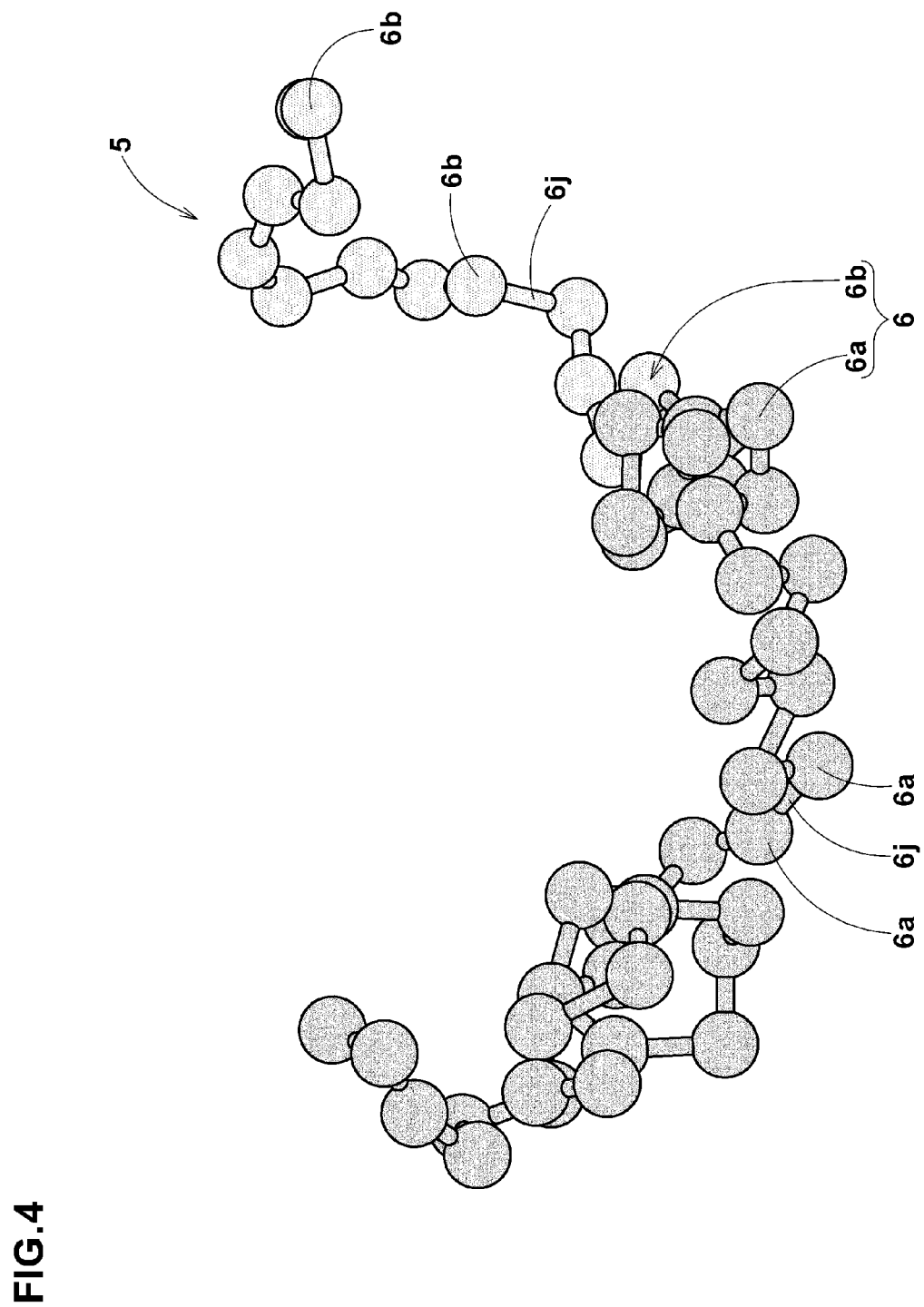
FIG. 4 is a diagram showing a polymer model.

In this step S2, as shown in FIG. 4, each polymer model 5 is defined to represent at least one polymer particle 6 preferably a plurality of polymer particles 6 of the high polymer material.

Incidentally, the polymer model 5 corresponds to numerical data necessary to deal with the high polymer material by the molecular dynamics. Such numerical data are entered and stored in the computer 1.

The polymer particles 6 of the polymer model 5 in this example include modified basal particles 6b and nonmodified particles 6a, and
different potentials (after-mentioned) are defined for the particles 6a and particles 6b.
Each of the particles 6a and 6b is a sphere having a certain diameter.

Between the particles 6a and 6b, there are provided joining chains 6j so as to keep them under restraint and to have a three dimensional structure like a straight-chain polymer.

Next, a simulation condition defining step S3 is implemented. In this step S3, simulation conditions necessary for executing the subsequent molecular dynamics (MD) calculation are set.

Figure 5:
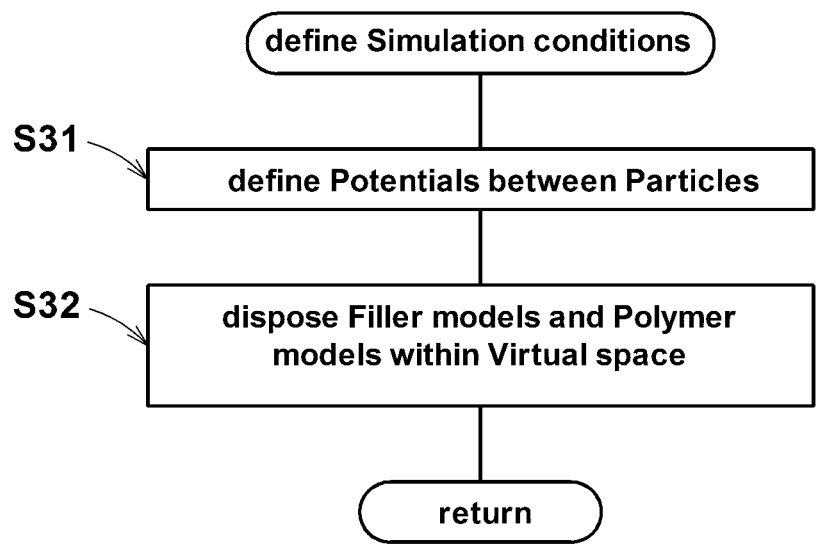
FIG. 5 is a flow chart of the simulation condition defining step.

FIG. 5 shows a flowchart of the simulation condition defining step S3.

Figure 6:
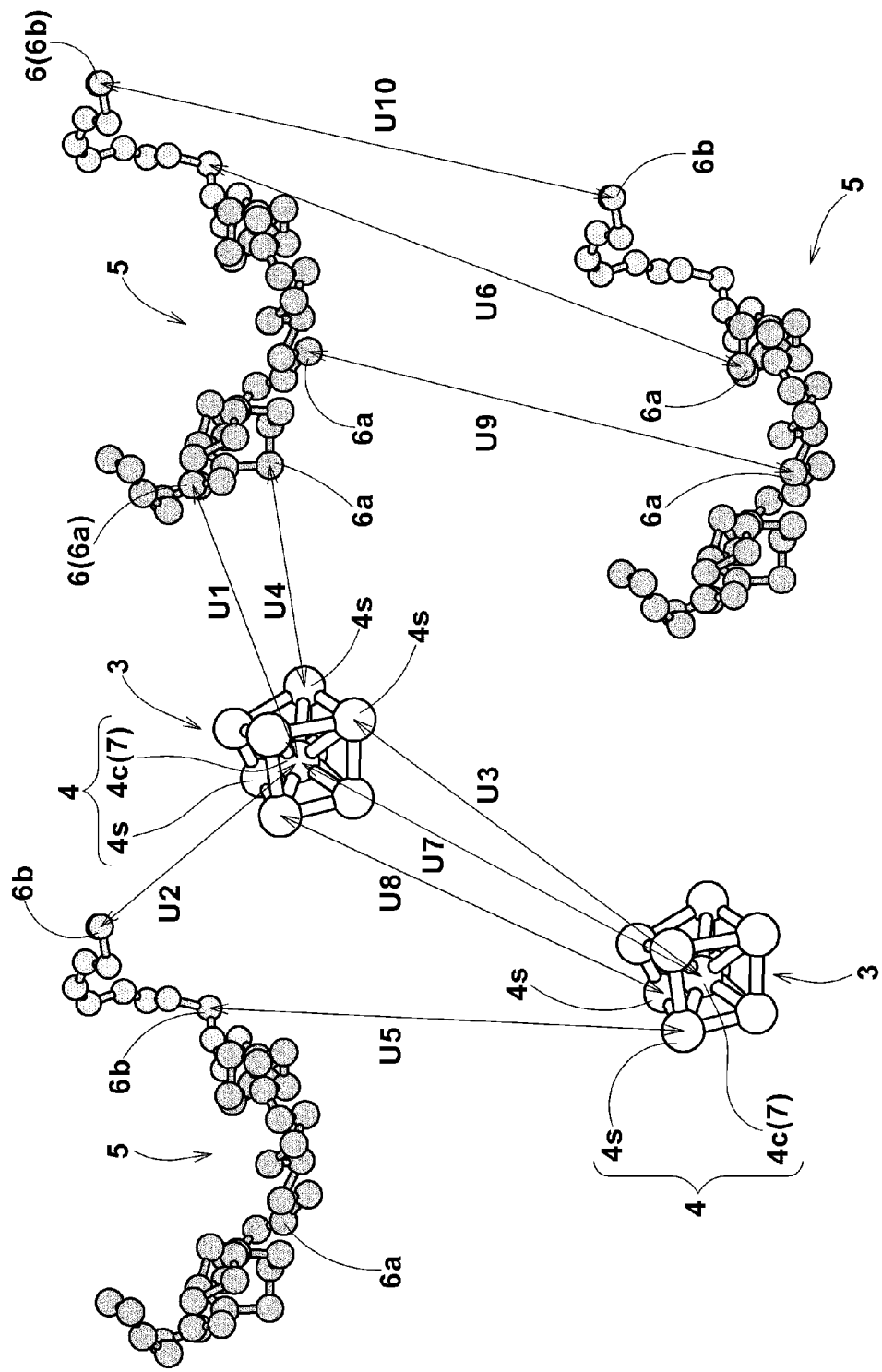
FIG. 6 is a diagram for explaining potentials between various particles inclusive of the filler particles and polymer particles.

In the step S3 in this embodiment, firstly, a potential defining step S31 is implemented. In this step S31, as shown in FIG. 6, potentials are respectively defined
between the filler particles 4c, 4s of a filler model 3 and the filler particles 4c, 4s of another filler model 3,
between the filler particles 4c, 4s of a filler model 3 and the polymer particles 6a, 6b of a polymer model 5, and
between the polymer particles 6a, 6b of a polymer model 5 and the polymer particles 6a,6b of another polymer model 5.

The potentials are stored in the computer 1 as numerical data, and used to calculate a force between the two particles concerned. Here, the potential is a function of the distance between the concerned particles. The potential U is given by the following expression (2):

$$U = a_{ij}(1 - r_{ij}/r_c)^2/2$$

where
$a_{ij}$ is an invariable corresponding to the strength of the potential U defined between the particles concerned,
$r_{ij}$ is the distance between the centers of the particles concerned, and
$r_c$ is the cutoff distance predefined between the particles concerned.

with the expression (2), the potential U is defined such that a mutual interaction (in this embodiment, a repulsive force) occurs if the distance $r_{ij}$ is decreased under the predefined cutoff distance $r_c$. If the distance $r_{ij}$ is more than the cutoff distance $r_c$, the potential U is zero and no repulsive force occurs between the particles.

In this particular example, for the following combinations of two particles, potentials U1-U10 are defined:
particles 4c-6a: potential U1
particles 4c-6b: potential U2
particles 4c-4s: potential U3
particles 4s-6a: potential U4
particles 4s-6b: potential U5 particles 6a-6b: potential U6
particles 4c-4c: potential U7
particles 4s-4s: potential U8
particles 6a-6a: potential U9
particles 6b-6b: potential U10

As to the strength $a_{ij}$ of the potential, a treatise (J. Chem Phys. 107(11) 4423-4435 (1997)) proposes that the strength $a_{ij}$ of potential between particles of the same kind is set to be 25.

But, various researches made afterward (for example, Macromolcule vol. 39 6744 (2006)) suggest that the strength $a_{ij}$ of potential between particles of the same kind is set to be 50, and the strength $a_{ij}$ of potential between particles of the different kinds is set to be 72.

In this example, by reference to these values, the strength $a_{ij}$ of the potentials U1-U10 are set as follows.
potential U1: $a_{ij}=72$
potential U2: $a_{ij}=25$
potential U3: $a_{ij}=50$
potential U4: $a_{ij}=72$
potential U5: $a_{ij}=25$
potential U6: $a_{ij}=72$
potential U7: $a_{ij}=50$
potential U8: $a_{ij}=50$
potential U9: $a_{ij}=50$
potential U10: $a_{ij}=50$ As above, the strength $a_{ij}(=25)$ of the potential U2, U5 between the modified basal particle 6b of the polymer model 5 and the filler particle 4c, 4s of the filler model 3 is set to be smaller than the strength $a_{ij}(=72)$ of the potential U1, U4 between the nonmodified particle 6a of the polymer particle 6 and the filler particle 4c, 4s of the filler model 3, therefore, in comparison with the nonmodified particle 6a, the modified basal particle 6b is decreased in the repulsive force.

Such modified basal particle 6b is increased in the affinity to the filler particle 4c, 4s, and therefore can simulate a denaturizing agent actually added in the high polymer material. Accordingly, by incorporating such modified basal particles 6b in the polymer model 5, the dispersion of the filler models 3 in the polymer models 5 can be changed, and it becomes possible to simulate a modified polymer.

In the expression (2), the cutoff distance $r_c$ is defined for each of the potentials U1-U10 as follows.
potential U1: $r_c=3$
potential U2: $r_c=3$
potential U3: $r_c=3$
potential U4: $r_c=1$
potential U5: $r_c=1$
potential U6: $r_c=1$
potential U7: $r_c=5$
potential U8: $r_c=1$
potential U9: $r_c=1$
potential U10: $r_c=1$ According to the present invention, one of the filler particles 4 of each filler model 3 is defined as a most influential particle 7.
Further, the following three different cutoff distances $r_c$ are predefined:
a largest cutoff distance used between the most influential particle 7 of a filler model 3 and the most influential particle 7 of another filler model 3;
a smallest cutoff distance used between any particle 4 other than the most influential particle 7 of a filler model 3 and any particle 4 other than the most influential particle 7 of another filler model 3; and
a middle cutoff distance used between the most influential particle 7 of a filler model 3 and any particle 4 other than the most influential particle 7 of another filler model 3.

In this embodiment, the center filler particle 4c of each filler model 3 is defined as the most influential particle 7. Therefore, for example as shown in FIG. 6, the cutoff distance $r_c$ used for the potential (for example U7) between the center filler particle 4c of a filler models 3 and the center filler particle 4c of another filler model 3 is set to be larger than the cutoff distance $r_c$ used for the potential (for example, U8) between the surface filler particle 4s of a filler model 3 and the surface filler particle 4s of another filler model 3.

The most influential particle 7 is a filler particle relating to the largest cutoff distance. Therefore, in a filler model 3, a potential from the outside of the filler model 3 acts on the most influential particle 7 (center filler particle 4c) prior to any other filler particles (surface filler particles 4s). Accordingly, the most influential particle 7 of the filler model 3 influences the motion of the filler model 3. Therefore, in the molecular dynamics calculation, it is possible to take the most influential particle 7 as the representative point of the filler model 3.

If migrations of the most influential particles 7 are increased, the filler models 3 are considered as being dispersed widely.

Figure 7:
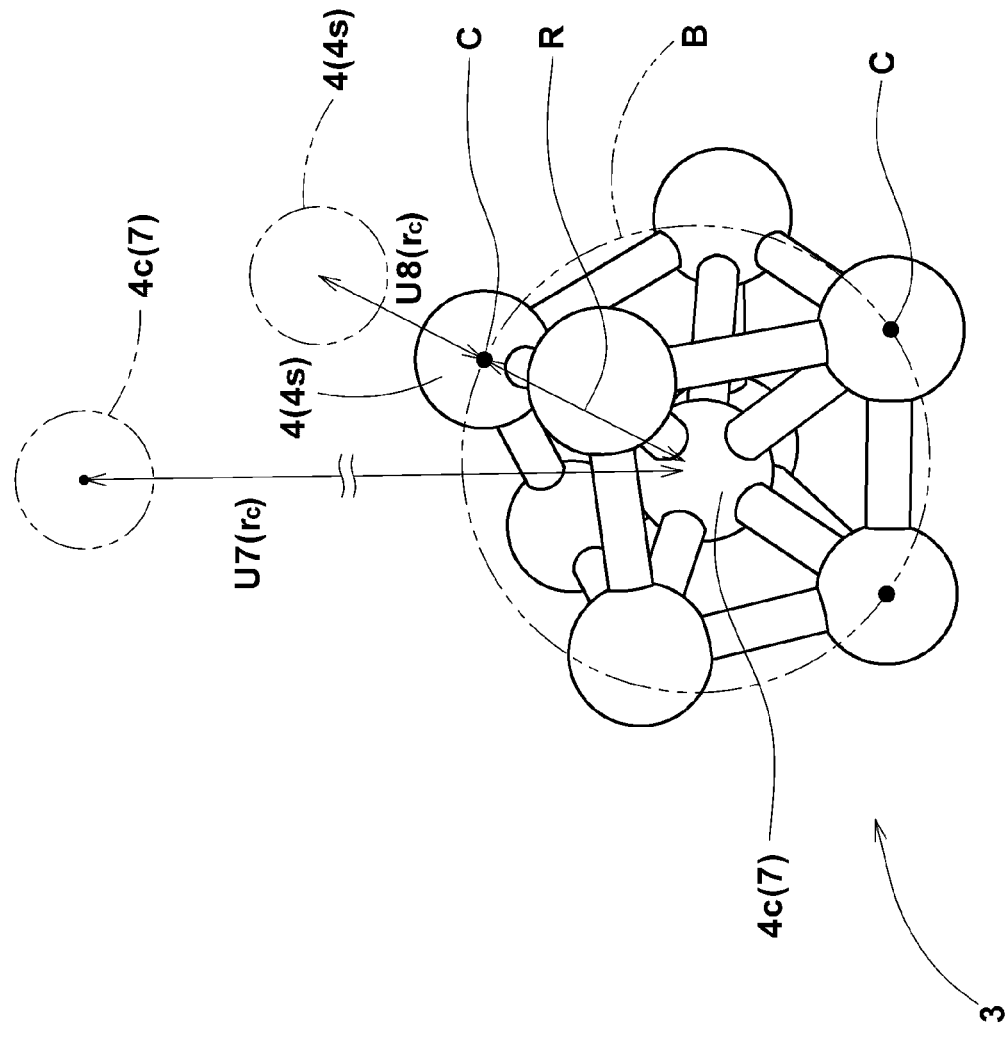
FIG. 7 is a diagram for explaining the cutoff distances between the filler particles.

It is desirable that, as shown in FIG. 7, the large cutoff distance $r_c$ (potential U7) used between the most influential particles 7 and 7 (i.e. between the center filler particles 4c and 4c) is set to be more than the sum ($r_c+R$) of the small cutoff distance $r_c$ (potential U8) between the particles 4 other than the most influential particle 7 (i.e. the surface filler particles 4s and 4s) and the radius R of the above-mentioned spherical surface B in order to assure that the potential acts on the most influential particle 7 prior to any other filler particles.

Between the most influential particles 7, the potential (e.g. U7) acts radially. Therefore, in the molecular dynamics calculation, the computer 1 can treat the filler models 3 as spheres like the actual filler.

Figure 8:
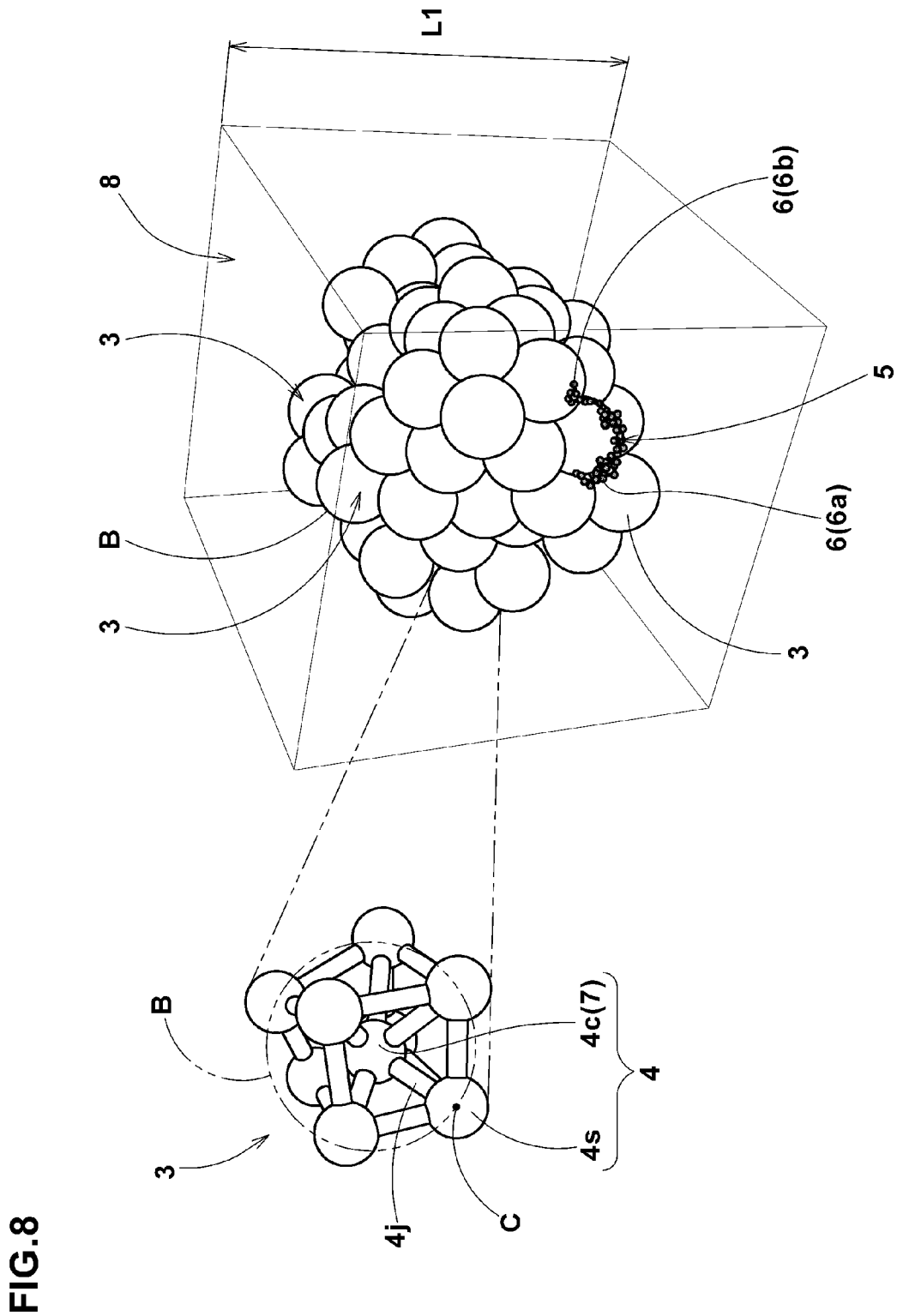
FIG. 8 is a perspective diagram for explaining a virtual space in which filler models and polymer models are disposed.

Next, as shown in FIG. 8, the filler models 3 and the polymer models 5 are disposed in a virtual space 8 having a predetermined volume. (step S32)

The virtual space 8 corresponds to a minute fraction of the actual high polymer material, e.g. polymer as the analysis object.

In this embodiment, the shape of the virtual space 8 is a regular hexahedron whose each side has a length L1 of from 20 to 40[$\sigma$] for example. [$\sigma$] is unit of length.

In the virtual space 8, for example, 500 to 1500 filler models 3 and 1000 to 3000 polymer models 5 are initially randomly disposed.

Next, a simulation step S4 is implemented. In this step S4, a molecular dynamics calculation is performed.

In the molecular dynamics calculation, assuming that all of the filler models 3 and the polymer models 5 in the virtual space 8 follow the classical dynamics, the calculation is made according to Newton's equation of motion for a given time period, and the motion of each of the filler particles 4c and 4s and the polymer particles 6a and 6b is tracked at each time step during the time period.

In this embodiment, the molecular dynamics calculation is continued until the initial placement of the filler models 3 and polymer models 5 which is artificial, becomes not artificial (structure relaxation).

As an example, when the number of the time steps reaches to a predetermined number (for example 500 to 300000), the molecular dynamics calculation is ended.

During making the molecular dynamics calculation, the number of all the particles existing in the system or the virtual space 8 and the volume and temperature of the system are kept constant.

Next, based on results obtained in the simulation step S4, the dispersion state of the filler models 3 is output for example as 2D or 3D images. (outputting step S5)

Figure 9:
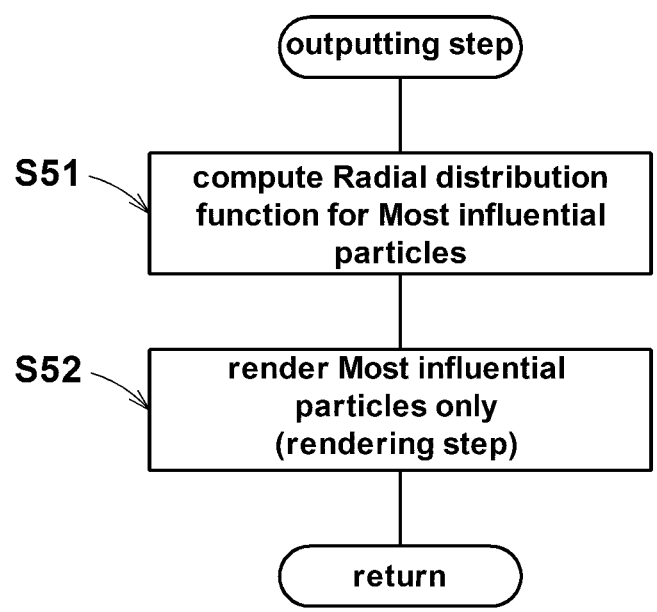
FIG. 9 is a flow chart of the outputting step.

FIG. 9 shows a flowchart of the outputting step S5. In the step S5 in this embodiment, firstly, a step S51 of computing a radial distribution function of the most influential particles 7 is implemented.

Figure 10:
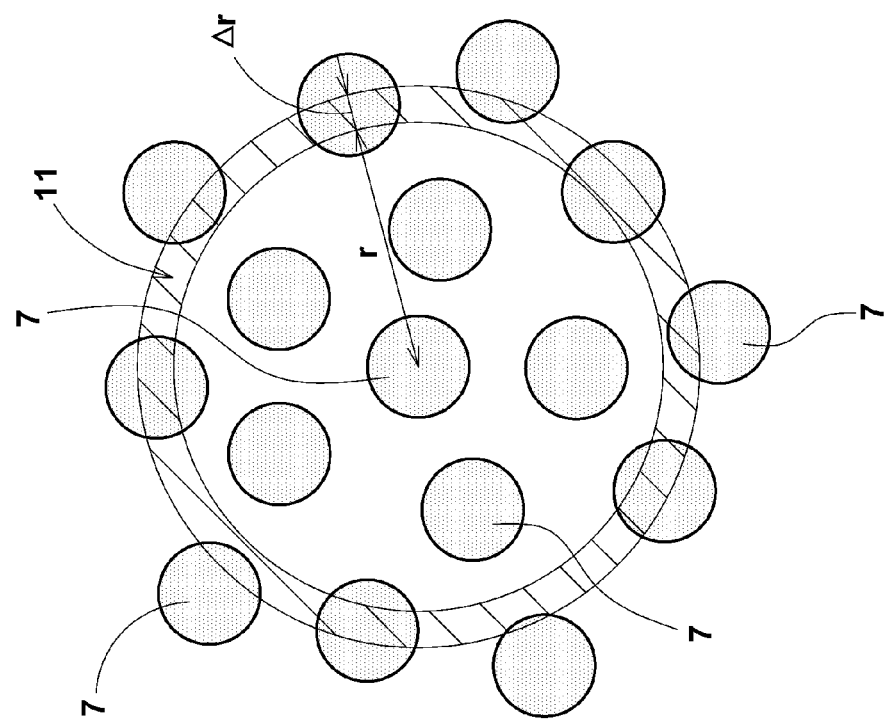
FIG. 10 is a diagram for explaining the radial distribution function.

Here, the radial distribution function g(r) is a probability density function which figures out the probability (g) that another most influential particle 7 exists at a distance (r) from a most influential particle 7 as shown in FIG. 10. The radial distribution function g(r) is given by the following expression (3):

$$g(r) = \langle n(r) \rangle / 4pir^2 \Delta r \rho \qquad (3)$$

where n(r) is the number of the most influential particles 7 existing between a distance (r) and a distance (r+Δr) from a most influential particle 7, in other words, existing in a spherical shell 11 defined between two concentric spherical surfaces of a radius (r) and a radius (r+Δr) whose centers coincide with the center of a most influential particle 7, ⟨n(r)⟩ is the value obtained by averaging the n(r) over all of the most influential particles 7 over the given time period of the molecular dynamics calculation, 4 pi r^2Δr is the volume of the spherical shell 11, pi is the circle ratio, ρ is the number density of the most influential particles 7 in the entire calculation system, namely, in the virtual space 8.

Figure 11:
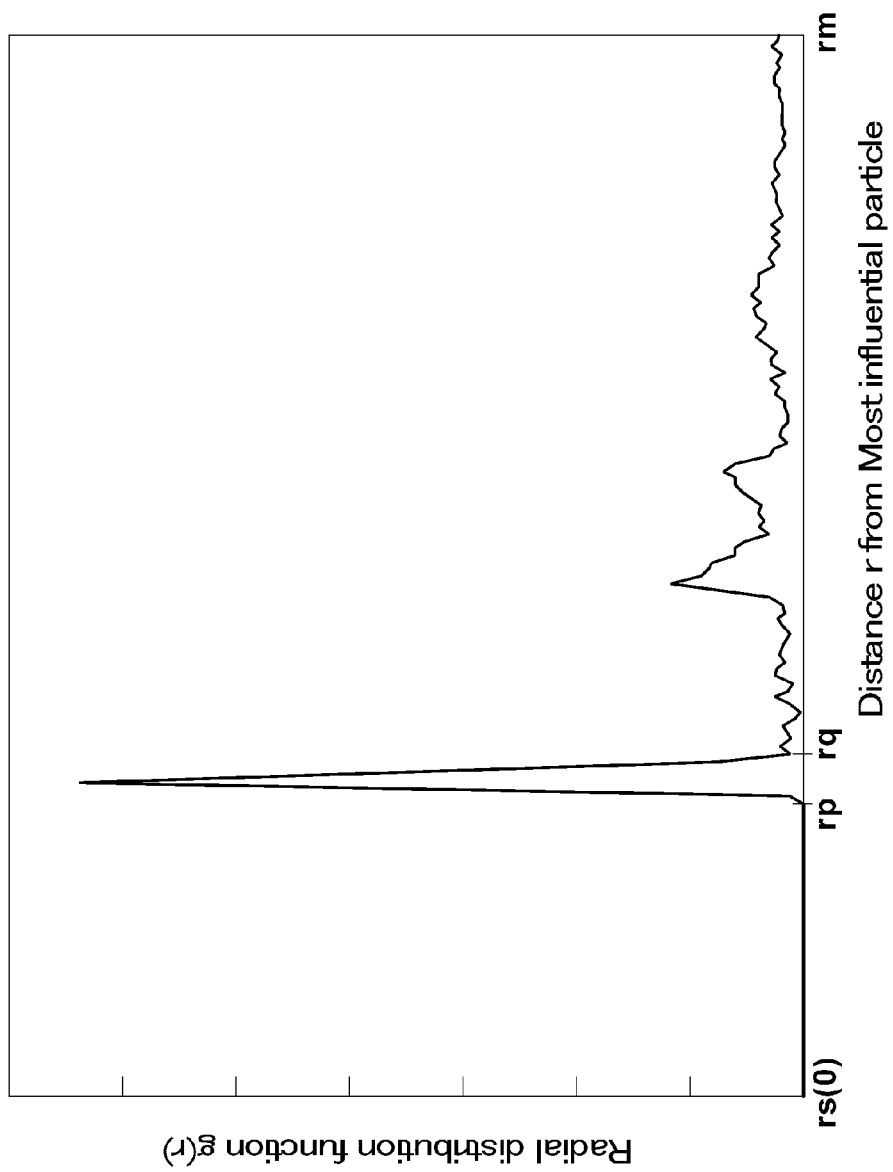
FIG. 11 is a graph of the radial distribution function.

FIG. 11 shows the radial distribution between the most influential particles 7 in this example obtained by the use of the expression (3).

From such radial distribution, the possible shortest distance between two most influential particles 7 and 7 when these are most approached to each other, can be obtained as the distance rp at which the value of the radial distribution function g(r) first becomes not zero in the course from the minimum value rs (zero) to the maximum value rm of the distance r.

FIG. 11 show that the distribution becomes almost uniform from a point rq off the peak toward the maximum value rm to the maximum value rm. Such distribution means that the filler models 3 are dispersed evenly in the virtual space 8.

Thus, by computing the radial distribution function g(r) for the most influential particles 7 (center filler particles 4c in this embodiment), it is possible to know the dispersion state of the filler models 3.

As to the range of the distance r set in order to calculate the radial distribution function, it is desirable that, in order to limit the distance r within the virtual space 8 and thereby to prevent too much increase in the computational cost, the minimum distance rs is set to zero, and the maximum distance rm is set to one half of the length L1 of a side of the virtual space 8 which side is not longer than any other side. (FIG. 8)

The acquisition intervals (of the distance r) of the radial distribution function g(r) are preferably set to a value not more than 1/5 of the maximum distance (rm), more preferably not more than 1/10 of the maximum distance (rm), to increase the degree of precision of the obtained radial distribution. If the acquisition intervals are too small, however, the computational cost increases. Therefore, the acquisition intervals are preferably not less than 1/100 of the maximum distance (rm).

Next, a rendering step S52 is implemented. In the rendering step S52, with respect to the filler models 3 existing in the virtual space 8, only the most influential particles 7 are rendered. In this embodiment, therefore, the surface filler particles 4s of the filler models 3 are hidden.

Figure 12:
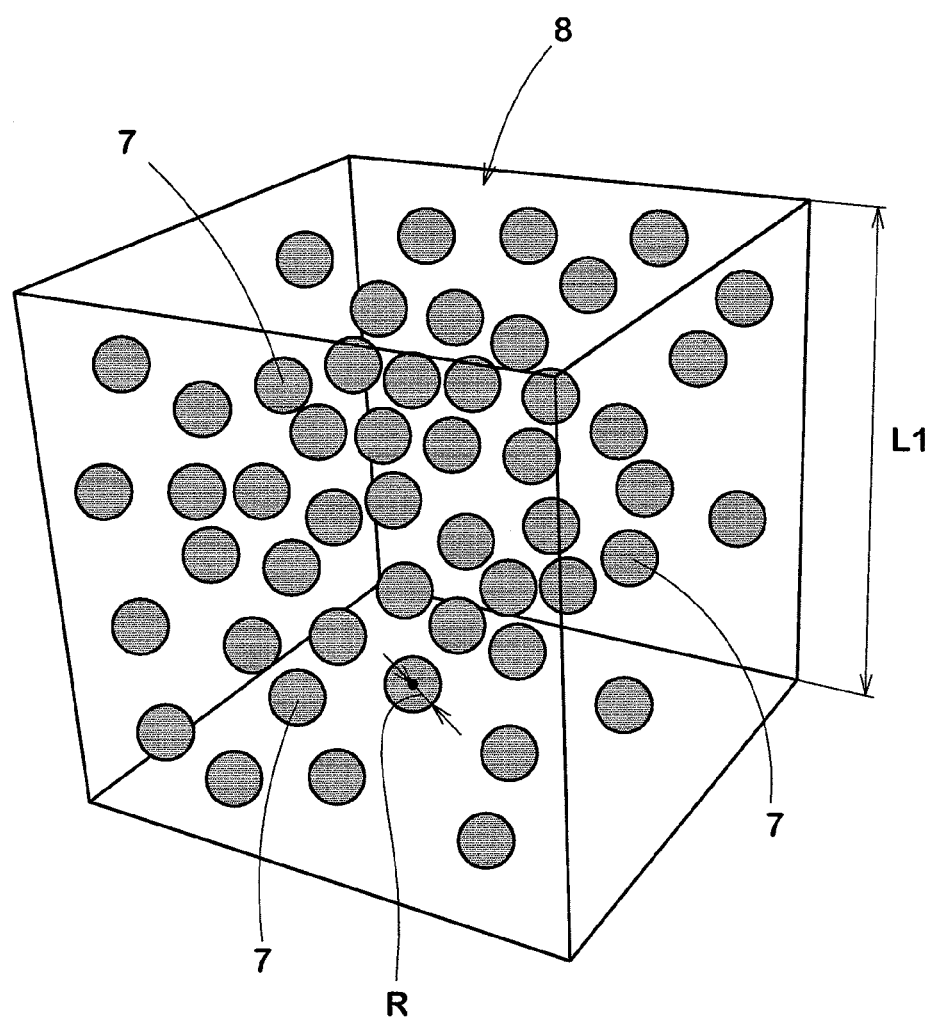
FIG. 12 is a 3D image obtained by rendering only the most influential particles in the virtual space.

In this embodiment, further, the polymer models 5 are also hidden. Therefore, in the rendered image regardless of 2D or 3D, as shown in FIG. 12, only the most influential particles 7 are shown in the virtual space 8. As a result, the filler dispersion state can be recognized easily. Further, the computational time required to render the filler dispersion state can be greatly reduced.

Figure 13:
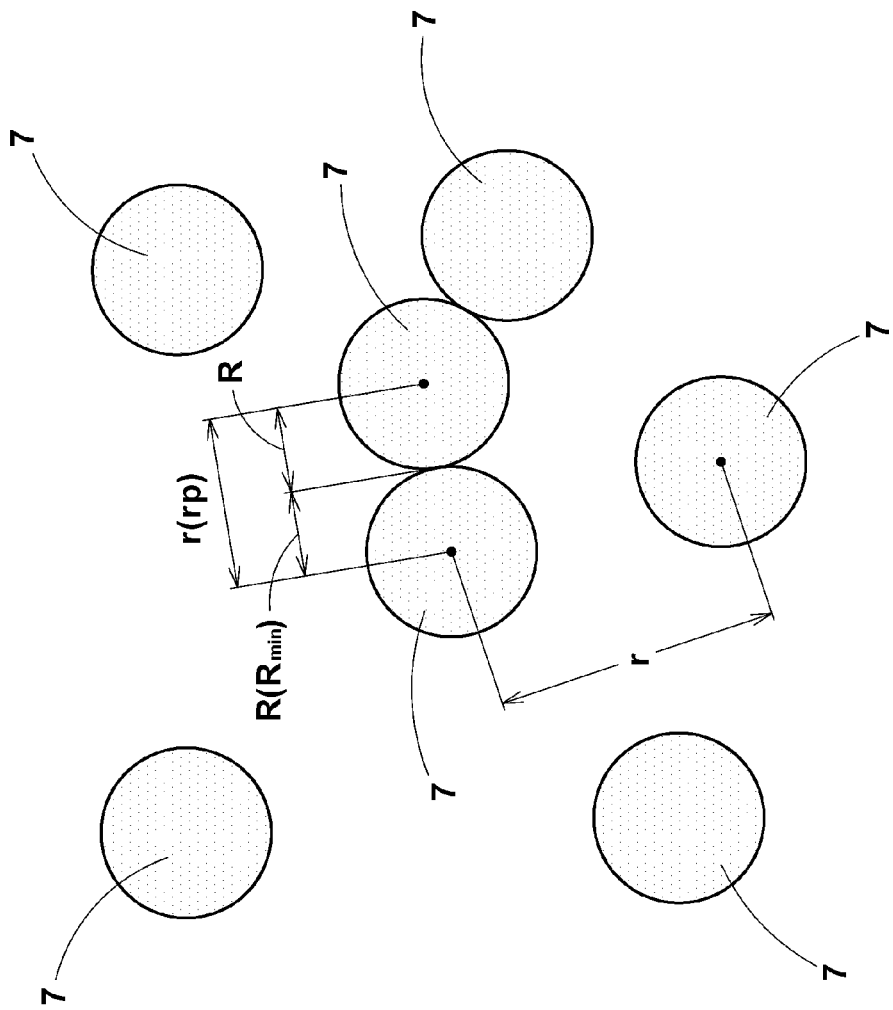
FIG. 13 is a diagram for explaining arrangements of the most influential particles.

The most influential particle 7 is rendered as a sphere having the radius R to emulate the shape of the filler model 3. In this embodiment, the radius R is limited in a range between Rmin and Rmax. The lower limit Rmin is set to one half of the above-mentioned shortest distance rp of the radial distribution function g(r). Therefore, the nearest two most influential particles 7 becomes in contact with each other as shown in FIG. 13 or overlapped with each other. Thereby, it is possible to simulate an aggregational state in which the filler models 3 are densely arranged.

when the distance r between the most influential particles 7 and 7 is more than one half of the radius R, the most influential particles 7 and 7 are rendered as separating from each other, to show a filler dispersion state.

Figure 14:
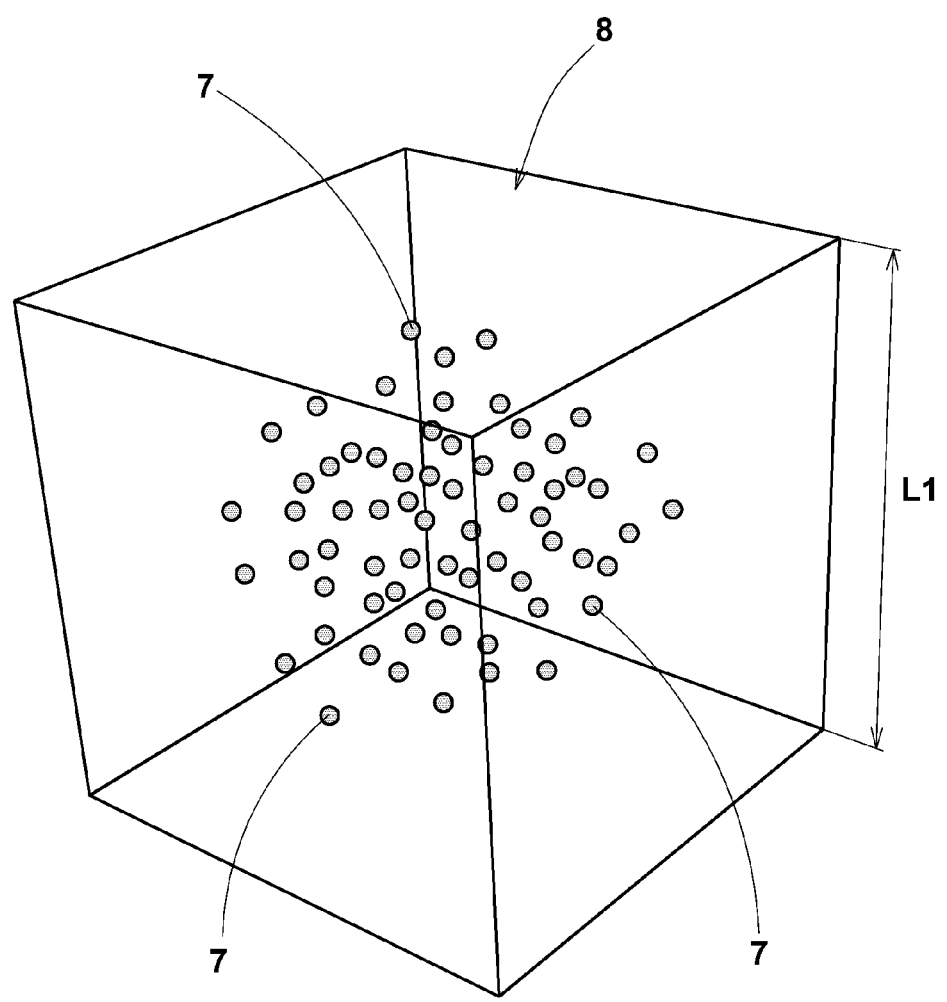
FIG. 14 is a 3D image obtained by rendering only the most influential particles under a condition such that the radius R is less than the lower limit Rmin.

If the radius R becomes less than the lower limit Rmin, even in the aggregational state, as shown in FIG. 14, the nearest two most influential particles 7 and 7 separate from each other, therefore, it becomes difficult to recognize the aggregational state.

In this embodiment, the upper limit Rmax is set to a value obtained by the following expression (1):

$$R\max = (V/N)^{1/3}/2 \qquad (1)$$

wherein

V is the volume of the virtual space 8, and

N is the number of the most influential particles in the virtual space 8.

Figure 15:
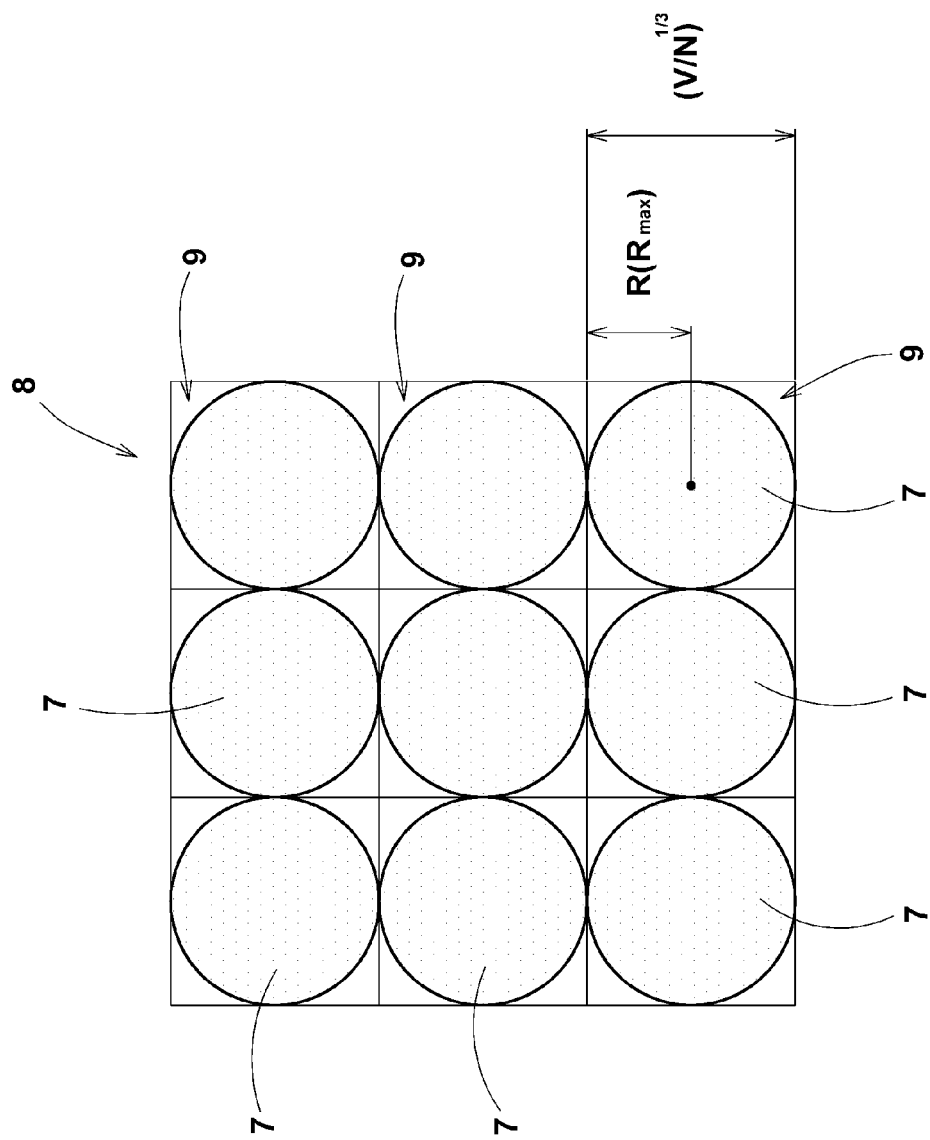
FIG. 15 is an elevation view of a virtual space in which most influential particles are uniformly dispersed in rows and columns.

FIG. 15 shows an elevation view of the virtual space 8. The term V/N corresponds to the volume of each of spacial elements 9 of the virtual space 8 divided by the number (for example 27) of the most influential particles.

When the most influential particles 7 are arranged in the spacial elements 9 one by one, such state is a state of the filler models 3 uniformly dispersed in the virtual space 8.

(Uniformly Dispersed State)

When the volume V/N of a spacial element 9 is raised to the one-third power, the length of one side of the spacial element 9 can be obtained on the assumption that the spacial element 9 is a regular hexahedron.

The 1/2 of the length $(V/N)^{1/3}$ of one side corresponds to the value of the radius R of the most influential particle 7 when the two most influential particles are circumscribed with each other under the uniformly dispersed state.

By setting the upper limit Rmax to the above-mentioned value, the adjoining most influential particles 7 under the uniformly dispersed state, can be prevented from overlapping each other when they are rendered. Thus, the filler dispersion state can be shown in such a way that a viewer can recognize the filler dispersion state easily.

Figure 16:
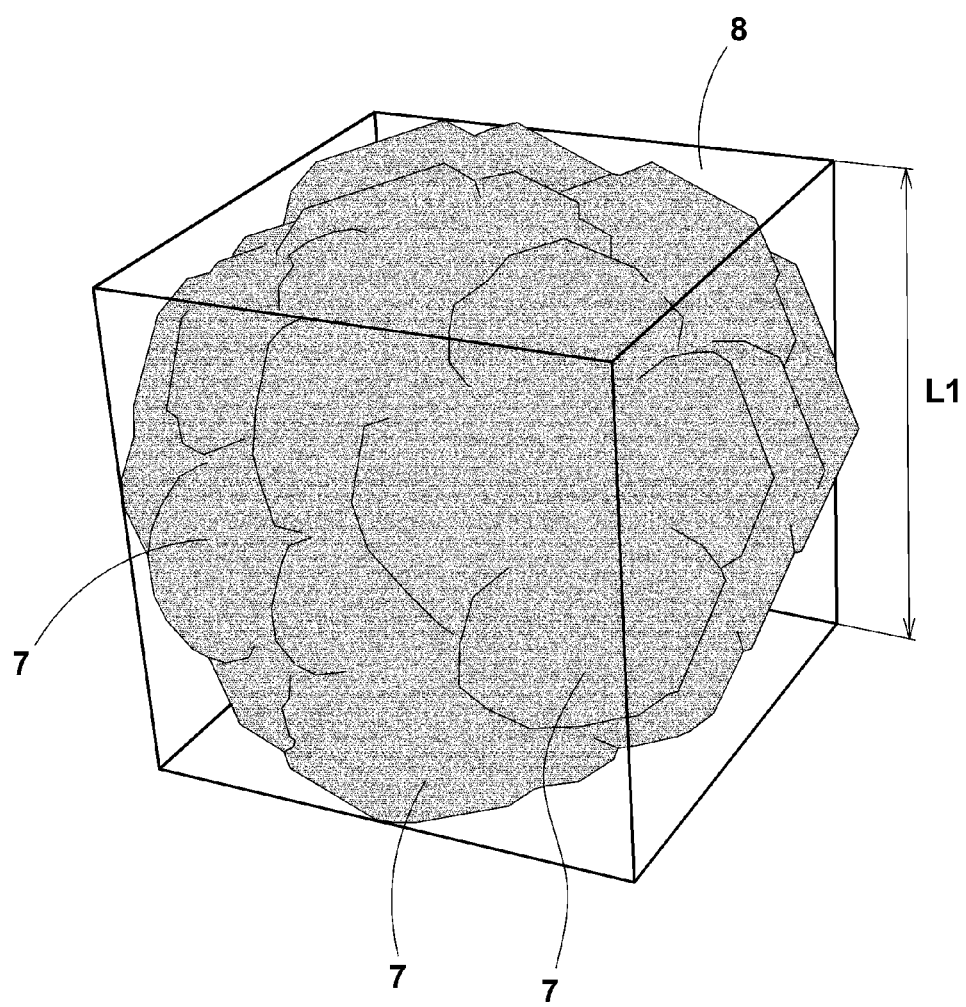
FIG. 16 is a 3D image obtained by rendering only the most influential particles under a condition such that the radius R is more than the upper limit Rmax.

If the upper limit Rmax is more than the value obtained by the expression (1), the adjoining most influential particles 7 under the uniformly dispersed state are overlapped with each other as shown in FIG. 16, therefore, it is difficult for the viewer to recognize the filler dispersion state exactly.

Next, it is judged whether the dispersion state of the filler models 3 is good or not. (step S6)

In this step S6, according to the image (FIG. 12) of the most influential particles 7 created in the rendering step S52, the filler dispersion state is evaluated with the unaided eye of an operating personnel.

In this embodiment, if the operating personnel judges the dispersion state of the filler models 3 as good, the simulation is ended.

On the other hand, if the operating personnel judges the dispersion state as not good, taking the image of the most influential particles 7 into consideration, the conditions previously set on the filler models 3 and the polymer models 5 are changed, and again the simulation is implemented. Such operation is repeated to find out conditions in which the filler models 3 are well dispersed.

The invention claimed is:

1. A computerized method for simulating the dispersion of fillers in a high polymer material, comprising:
    a filler model defining step in which filler models of the fillers are defined, wherein each of the filler models represents a plurality of filler particles,
    a polymer model defining step in which polymer models of the high polymer material are defined, wherein each of the polymer models represents one or more polymer particles,
    a potential defining step in which, between the particles inclusive of the filler particles and the polymer particles, potentials such that when the distance between the concerned particles is decreased under a predefined cutoff distance, a mutual interaction occurs therebetween, are defined, wherein one of the filler particles in each filler model is defined as a most influential particle for which a largest cutoff distance is defined,
    a simulation step in which a molecular dynamics calculation is performed on the polymer models and the filler models placed in a predetermined virtual space, and
    an outputting step in which, based on results obtained through the simulation step, the dispersion of the filler models is output,
    wherein the outputting step includes a rendering step in which the filler particles other than the most influential particles are hidden whereas the most influential particles of the filler models in the virtual space are rendered to present the state of the dispersion of the filler models.

2. The computerized method according to claim 1, wherein
    the outputting step further includes, before the rendering step, a step in which a radial distribution function of the most influential particles of the filler models is calculated, and
    in the rendering step, each of the most influential particles is rendered as a sphere having a radius R of not less than a value Rmin and not more than a value Rmax, wherein
    the value Rmin is one half of a shortest distance between the most influential particles obtained from the radial distribution function, and
    the value Rmax is given by the following expression (1)

$$R\max = (V/N)^{1/3}/2 \quad (1)$$

where
    V is the volume of the virtual space, and
    N is the number of the most influential particles existing in the virtual space.

3. The computerized method according to claim 2, wherein
    the filler particles of each filler model are a single center filler particle and at least four surface filler particles whose centers are positioned on a spherical surface whose center coincides with a center of the center filler particle,
    equilibrium lengths are respectively defined between the center filler particle and the surface filler particles and between the surface filler particles, and
    the center filler particle is the most influential particle.

4. The computerized method according to claim 1, wherein
    the filler particles of each filler model are a single center filler particle and at least four surface filler particles whose centers are positioned on a spherical surface whose center coincides with a center of the center filler particle,
    equilibrium lengths are respectively defined between the center filler particle and the surface filler particles and between the surface filler particles, and
    the center filler particle is the most influential particle.

5. The computerized method according to claim 4, wherein
    the cutoff distance between the center filler particles is larger than the sum of the radius of the spherical surface and the cutoff distance between the surface filler particles.

* * * * *